United States Patent
Mauch et al.

(10) Patent No.: US 8,101,091 B2
(45) Date of Patent: Jan. 24, 2012

(54) INTRODUCER ASSEMBLY AND METHOD FOR FORMING AN INTRODUCER ASSEMBLY

(75) Inventors: Grant A Mauch, Delano, MN (US); Brian Anderson, Buffalo, MN (US); Kevin Pietsch, Greenfield, MN (US); Steve Moreland, Aitkin, MN (US)

(73) Assignee: Greatbatch Ltd., Clarence, NY (US)

( * ) Notice: Subject to any disclaimer, the term of this patent is extended or adjusted under 35 U.S.C. 154(b) by 1178 days.

(21) Appl. No.: 11/695,452

(22) Filed: Apr. 2, 2007

(65) Prior Publication Data

US 2008/0082120 A1    Apr. 3, 2008

Related U.S. Application Data

(63) Continuation-in-part of application No. 11/537,919, filed on Oct. 2, 2006, now abandoned.

(51) Int. Cl.
*C03C 15/00*    (2006.01)

(52) U.S. Cl. .............. 216/34; 216/2; 216/8; 216/33; 216/41; 216/52; 216/83

(58) Field of Classification Search .............. 216/2, 8, 216/33, 34, 41, 52, 83
See application file for complete search history.

(56) References Cited

U.S. PATENT DOCUMENTS

| | | | |
|---|---|---|---|
| 5,098,392 A | 3/1992 | Fleischhacker et al. | |
| 5,167,634 A | 12/1992 | Corrigan, Jr. et al. | |
| 5,445,624 A * | 8/1995 | Jimenez | 604/525 |
| 6,083,207 A | 7/2000 | Heck | |
| 6,712,791 B2 * | 3/2004 | Lui et al. | 604/167.04 |
| 6,918,927 B2 * | 7/2005 | Bates et al. | 623/1.15 |
| 7,172,575 B2 | 2/2007 | El-Nounou et al. | |
| 7,422,571 B2 | 9/2008 | Schweikert et al. | |
| 2001/0049499 A1 | 12/2001 | Lui et al. | |
| 2003/0163139 A1 | 8/2003 | Graf | |
| 2004/0098020 A1 | 5/2004 | Nardeo | |
| 2005/0010238 A1 | 1/2005 | Potter et al. | |
| 2005/0021002 A1 | 1/2005 | Deckman et al. | |
| 2005/0049628 A1 * | 3/2005 | Schweikert et al. | 606/198 |
| 2005/0061771 A1 | 3/2005 | Murphy | |
| 2005/0096688 A1 | 5/2005 | Slazas et al. | |
| 2008/0082056 A1 | 4/2008 | Mauch et al. | |
| 2008/0243165 A1 | 10/2008 | Mauch et al. | |

FOREIGN PATENT DOCUMENTS

| | | |
|---|---|---|
| WO | WO-9714456 A1 | 4/1997 |
| WO | WO-0236179 A2 | 5/2002 |
| WO | WO-03026718 A1 | 4/2003 |
| WO | WO-2005025661 A3 | 3/2005 |

(Continued)

OTHER PUBLICATIONS

"U.S. Appl. No. 11/537,919, Non-Final Office Action Mailed Oct. 8, 2008", 10 pages.

(Continued)

*Primary Examiner* — Nadine Norton
*Assistant Examiner* — Christopher Remavege
(74) *Attorney, Agent, or Firm* — Michael F. Scalise

(57) ABSTRACT

An introducer assembly includes a sheath having a sheath proximal end and distal end, and a passage therethrough. The introducer assembly further includes a handle assembly that is mechanically and/or bonded coupled with a tubular sheath.

28 Claims, 3 Drawing Sheets

FOREIGN PATENT DOCUMENTS

| | | |
|---|---|---|
| WO | WO-2006036653 A2 | 4/2006 |
| WO | WO-2006036653 A3 | 4/2006 |
| WO | WO-2008042390 A2 | 4/2008 |
| WO | WO-2008042390 A3 | 4/2008 |

OTHER PUBLICATIONS

"U.S. Appl. No. 11/537,919, Response filed Jan. 8, 2009 to Non Final Office Action mailed Oct. 8, 2008", 10 pages.

"European Application Serial No. 08251071.0, European Search Report mailed Jun. 13, 2008", 15 pages.

"International Application Serial No. 08251061.1, Extended European Search Report mailed Jul. 1, 2008", 7 pages.

"International Application Serial No. PCT/US2007/021188, International Search Report mailed Jun. 30, 2008", 6 pages.

"International Application Serial No. PCT/US2007/021188, Written Opinion mailed Jun. 30, 2008", 6 pages.

\* cited by examiner

INTRODUCER ASSEMBLY AND METHOD FOR FORMING AN INTRODUCER ASSEMBLY

RELATED APPLICATION

This application is a continuation-in-part of U.S. application Ser. No. 11/537,919 filed Oct. 2, 2006 now abandoned, which is incorporated herein by reference and made a part hereof.

TECHNICAL FIELD

Introducers and introducing assemblies, and more specifically an introducer assembly including a bonded sheath assembly.

BACKGROUND

Introducer devices provide for access to the vascular system and are employed for inserting medical devices such as catheters, guidewires, leads, infusion ports, dialysis ports, dialysis catheters, and others. A typical procedure for gaining access to the central venous system or the arterial system with an introducer is the Seldinger Introduction Method. The Seldinger Method provides for insertion of a needle into the vasculature of a patient. Once the needle is in the vessel, the physician aspirates the needle to assure that the needle is in the vessel, and to draw out air present in the bore of the needle. The syringe is removed and discarded. A guide wire is inserted through the needle, and the needle is removed over the guide wire. The introducer, which includes a dilator and the sheath, is placed over the guidewire and inserted into the vessel. With the introducer and wire guide in the vessel, the dilator and wire guide are removed leaving only the sheath in the vessel. The desired medical device is implanted through the passage of the sheath.

The sheath is optionally removed from the medical device. Some removable sheaths are formed of lubricious materials with low coefficients of friction, which is difficult to effectively couple or seal with other components. Furthermore, the introducer device provides access to the vein or artery, and therefore control of bleeding and the intake of air is necessary, for example, through use of a valve.

Accordingly, what is needed is an introducer assembly which can effectively seal against a wide variety of instruments without inhibiting the throughput of the instrument, or damaging the instrument. What is also needed is an introducer assembly which does not distract or interfere with the implantation process.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1A:
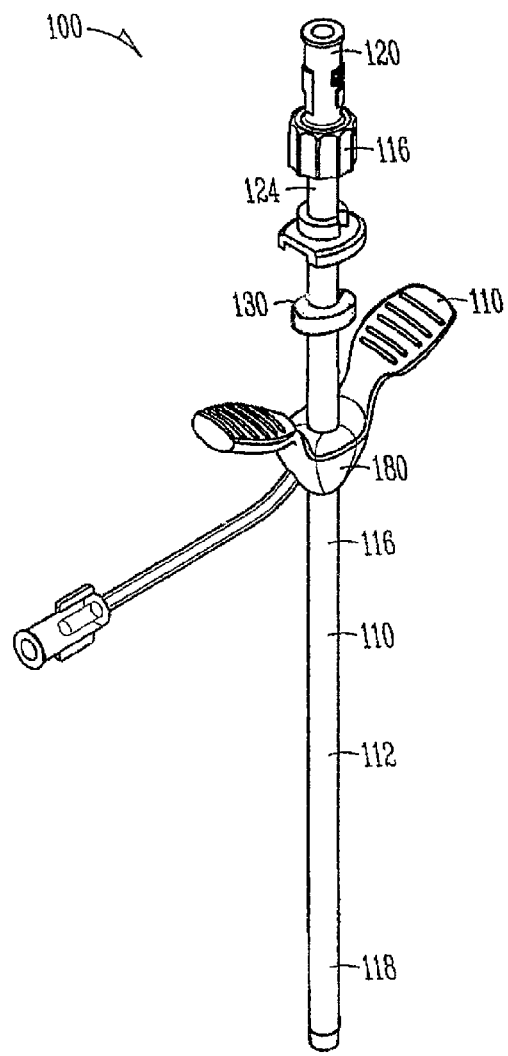
FIG. 1A illustrates a perspective view of an introducing assembly as constructed in accordance with at least one embodiment.
Figure 1B:
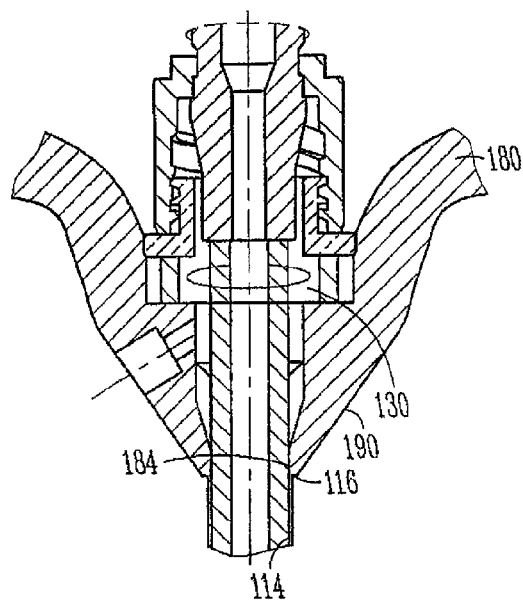
FIG. 1B illustrates a cross-sectional view of a portion of an introducing assembly as constructed in accordance with at least one embodiment.

An introducer assembly 100 is illustrated in FIGS. 1A and 1B. The introducer assembly includes a sheath assembly 110 having a sheath 112 with a passage 114 therethrough. The sheath 112 is coupled with a handle assembly 180 as further described below. The sheath 112 extends from a sheath proximal end portion 116 to a sheath distal end portion 118, and is defined in part by a longitudinal axis. Near the sheath distal end portion 118 is a tapered portion, allowing for a more tapered transition portion to taper to the dilator disposed therethrough.

The sheath 112 is formed of, in an example, fluorinated polymers such as, but not limited to, PTFE (PolyTetraFluoroEthylene), FEP (Fluorinated Ethylene-Propylene), or non-fluorinated polymers such as nylon, polyurethane, polyethylene, polyamide, polypropylene, or polyimide. These materials assist in provided lubricious surface proprieties. The sheath material, such as the PTFE, is molecularly oriented in its extruded state for optionally splitting the sheath. The molecularly oriented sheaths do not necessarily require an additional mechanical scoring operation to produce split lines. Instead, the oriented molecules allow the sheath 112 to naturally peel like a banana.

In a further option, the sheath 112 includes various types of sheaths, for instance, the sheath 112 can comprise a sheath which has a strengthening material, such as a strengthening braid of material. Alternatively, the sheath 112 includes a sheath which is modified to assist in preventing bends and/or kinks along the sheath. In a further option, the sheath 112 includes a co-extrusion of multiple units or different types of materials. In yet a further option, the sheath 112 includes a component having one or more coatings thereon. It should be noted the sheath 112 can be formed of combinations of one or more types of the sheaths.

The introducer assembly 100 further includes an instrument such as a dilator 120 that can be coupled with the sheath assembly 110, for example, with a rotatable coupler 116. For example, the rotatable coupler 116 includes a threaded portion that engages a projection or thread on the sheath assembly 110. The dilator 120 is removably disposed within a passage 114 of the sheath 112, and optionally is coaxial with the sheath 112. The sheath 112 includes a support diameter which is sized to receive a dilator 120 having a dilator diameter therethrough. It should be noted that other instruments such as leads and/or guidewires can be disposed through the sheath and sheath passage 114, as will further be described below. The dilator 120 extends from a dilator distal end to a dilator proximal end 124, where the dilator distal end is insertable into a patient, for example, over a needle or a guidewire. The dilator distal end optionally ends in a tapered end, allowing for ease of transition within tissue of a patient. The dilator proximal end 124 optionally includes features, such as a luer hub or threads, that allows for other devices to be coupled thereto.

In one embodiment, the handle assembly 180 and the sheath 112 are removable from around instruments disposed therein, such as a lead disposed with the sheath 112. For example, the sheath 112 is removable from around the instrument without having to slide or otherwise manipulate the introducer and/or the sheath over a proximal end of the instrument. In one option, the handle assembly 180 and/or the sheath 112 are removed from an outer perimeter along a cross-section of an instrument disposed therethrough.

The sheath 112 and/or the handle assembly 180, for example, can be removed from the instrument disposed therethrough in a number of different manners. For example, the sheath 112 can include structure integral therewith or non-integral that allows for the sheath 112 to be separated from around the instrument without damaging the instrument, and/or allows for the sheath 112 to be removed from the outer perimeter of the cross-section of the instrument. In some examples, the sheath 112 is coupled with a handle assembly 180, and the handle assembly 180 includes one or more tabs that are connected with the sheath 112 to tear the sheath 112 off of the instrument. In another example, the structure includes a tear strip, molecularly orientated material within the sheath, one or more openings in the sheath 112 allowing the sheath 112 to separate at one or more locations that each can be used alone or in combination to separate the sheath 112 from around the instrument. In another option, the sheath 112 is at least partially dissolvable within a body, allowing the sheath 112 to be removed from the instrument. In another option, a slitting or splitting device such as a slitter can be used to removed the sheath 112, where the sheath 112 is removed by slitting. In yet another option, the sheath further includes one, two or more tabs which can be used to separate the sheath away from the instrument. Further options include a pre-weakened or scored sheath, allowing for the sheath to be manually removed by tearing, separating, or slitting, for example. In yet another example, the sheath includes molecularly oriented material allowing for the sheath 112 to be removed from around the instrument.

The introducer assembly 100 optionally includes a valve 130 that is sealingly associated with the passage 114 of the sheath 112, allowing for substantial sealing of the passage 114. The valve 130 assists in preventing fluids to exit from a patient when the sheath 112 is disposed within the patient. The valve 130 assists in preventing fluids from exiting, yet permits passage of instruments through the valve 130, and in an option, substantially seals against the instruments that are disposed therethrough.

The valve 130 is coupled with a portion of the introducer 110, for example, within the handle assembly 180 of the introducer. The valve 130, in an option, is removable from around an outer cross-sectional perimeter of an instrument disposed through the introducer. For example, the valve 130 can include a mechanical weakening allowing for the valve 130 to slide off to the side of the instrument. Alternatively, the mechanical weakening can allow for the valve 130 to be torn or split away from the introducer. In yet another option, the valve 130 forms an adaptor that is attachable and removable by the user before, during, or after an implant procedure. For example, the user can remove or attach the valve assembly 130 with a fitting or other coupling.

Figure 3:
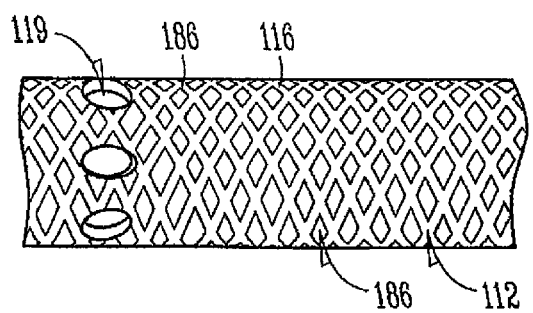
FIG. 3 illustrates side view of a portion of a sheath as constructed in accordance with at least one embodiment.

As mentioned above, the handle assembly 180 is coupled to the sheath 112, where they are coupled together at an interface 190. In an option, the interface 190 includes a proximal end portion 116 of the sheath 112 and/or a portion of the handle assembly 180, such as in inner diameter 184. In an option, the interface 190, such as the sheath proximal end portion 116 and/or the inner or outer diameter of the handle assembly 180 includes a surface treated portion 186, such as textured portion 186, for instance, as shown in FIG. 3. In an option, the textured portion extends around at least a portion of an outer circumference of the sheath 112. In another option, the surface treated portion 186 extends around the entire circumference of the sheath 112, at a proximal portion of the sheath 112.

The surface treated portion 186, such as the textured portion, is formed in an option by chemically etching, for example, the sheath proximal end portion 116. In an example, the sheath 112 is rinsed with a solution, such as alcohol. The sheath 112 and/or the handle assembly 180 are chemically etched with a solution such as, but not limited to sodium naphthalene/ethylene glycol dimethyl ether solution.

Figure 4:
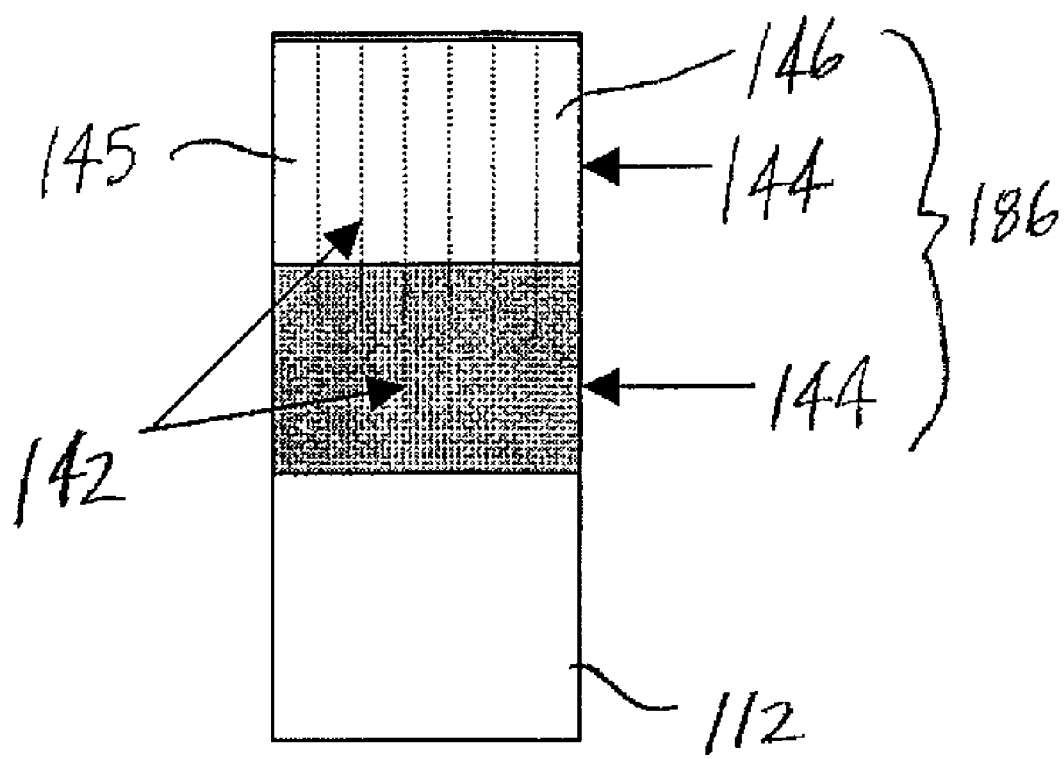
FIG. 4 illustrates side view of a portion of a sheath as constructed in accordance with at least one embodiment.

In another option, the surface treated portion 186 is formed by treating a first portion 142 with a first treatment, for example, mechanically treating the first portion 142, as shown in FIG. 4, the sheath 112, or media blasting the sheath 112, such as the proximal portion of the sheath 112. For example, the sheath 112 can be blasted by one or more of, alone or in combination, sodium bicarbonate (i.e. baking soda), sand, glass, mica, pumice, or dry ice (i.e. carbon dioxide). In yet another option, the surface treated portion 186 is formed by sanding or grinding the sheath 112, such as at a first portion 142 of the proximal portion of the sheath 112. In an option, the sanding or grinding of the sheath 112 is conducted with one or more of sand paper, grinding wheel, or a tooling stone.

Further options for forming the surface treated portion 186 or the first portion 142 include, but are not limited to, treating the surface treated portion 186 with abrasives in a carrier liquid. For instance, the surface treated portion 186 can be treated with a slurry including one or more of, alone or in combination, pumice, sand, mica, or glass.

In a further option, a second portion 144 of the interface is treated with a second treatment. The second treatment, such as a chemical etch, changes the surface characteristics of the sheath 112. For example, a contact angle of the sheath 112, measured with a goniometer, changes from a natural state (pre second treatment) of 80 degrees, to 70 degrees after it has been chemically etched. The reduction in surface angle allows molten plastic to better bond with the sheath 112. In an option, the second portion 144 is chemically etched with a solution such as, but not limited to sodium naphthalene/ethylene glycol dimethyl ether solution. In an option, the second treatment is done after the first treatment. In an option, the second portion 144 overlaps at least a portion of the first portion 142.

In another option, the second portion 144 occupies the same area as the first portion 142.

In yet another option, the second treatment, such as the chemical etch, is partially or entirely removed from the sheath 112. For instance, at least a portion 146 of the interface is treated with a third treatment to remove the second treatment such as the chemical etch. In an option, the portion 146 is disposed at the proximal end of the sheath 112. In an option, the third treatment includes mechanically treating the portion 146, such as by buffing, blasting, or otherwise treating the portion 146.

In still another option, the sheath 112 is masked prior to the second treatment, such as the chemical etch to control where the chemical etch occurs. For example, the sheath 112 can be masked at 145 to prevent chemical etch of the second treatment to occur at 145.

Figure 2:
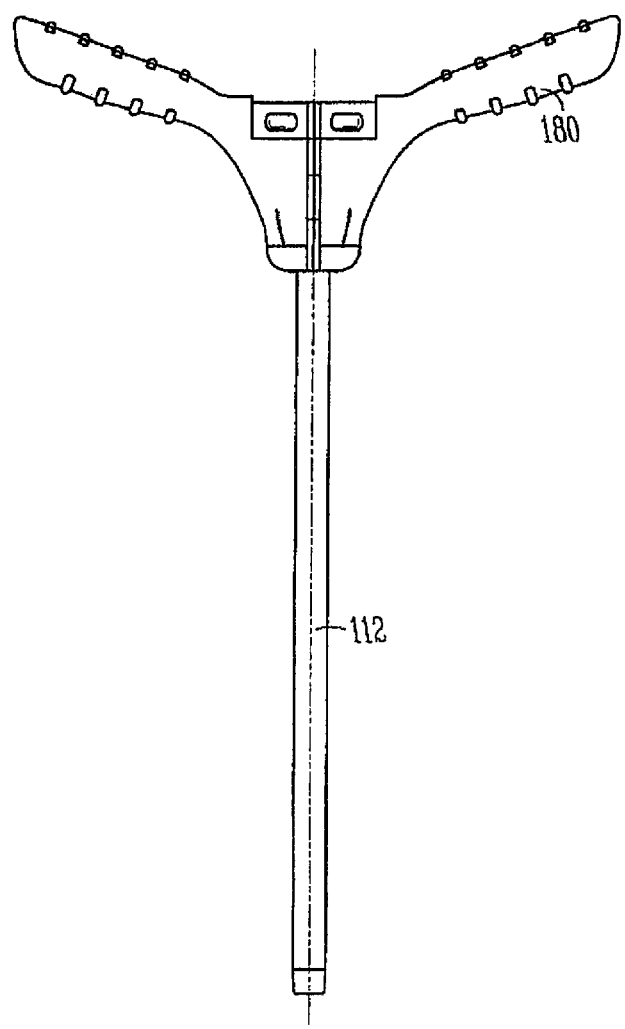
FIG. 2 illustrates side view of a portion of a sheath assembly as constructed in accordance with at least one embodiment.

Referring again to FIGS. 1B, 2, and 3, the handle assembly 180 is coupled to the sheath 112, in an example, by overmolding the handle assembly 180 over the sheath 112. In another option, the handle assembly 180 can be preformed, and coupled with the sheath 112 by applying energy to the handle assembly 180 and/or the sheath 112, such as applying heat. During the process, the material of the handle assembly 180 bonds with the sheath 112, and chemically bonds with the chemically etched portion. In a further option, one or more flow holes 119 are formed in the sheath 112, such as by punching, prior to coupling the handle assembly 180 thereto. The flow holes 119 allow for material of the handle assembly 180 to flow therethrough, and further permit a mechanical bond of the handle assembly 180 and the sheath 112.

Methods for forming the introducer assembly include the techniques discussed above. Furthermore, methods include a method for forming the introducer assembly includes forming a tube such as a fluorinated polymer tube, for example, by extruding the tube. The polymer tube forms a sheath extending from a sheath proximal end portion to a sheath distal end portion, and the sheath has a passage therethrough. The method further includes surface treating the sheath 112 at a proximal end to form a handle interface.

Referring to FIG. 4, the method includes surface treating a portion, such as a first portion 142 of the sheath 112 with a first treatment. In an option, the first treatment includes a mechanical treatment such as the mechanical treatments discussed herein, including, but not limited to media blasting the sheath 112 or texturizing the sheath 112. In another option, surface treating the interface portion or a first portion 142 of the sheath with the first treatment includes treating the sheath with one or more of, alone or in combination, sodium bicarbonate, sand, glass, mica, pumice, and/or dry ice. In a further option, surface treating with the first treatment includes media blasting the sheath with one or more of, alone or in combination, sodium bicarbonate, sand, glass, mica, pumice, and/or dry ice. In another option, surface treating the interface portion includes sanding and/or grinding the sheath. In yet a further option, surface treating includes treating the sheath with a slurry including one or more of, alone or in combination, pumice, sand, glass, and/or mica.

In a further option, the method includes treating a portion of the sheath 112, such as a second portion 144 of the sheath 112 with a second treatment. In an option, the second treatment includes chemically etching the second portion 144. In yet another option, a portion of the sheath 112 is masked prior to the second treatment, such as the chemical etching. For instance, the area at 145 can be masked prior to the chemical etching. In an option, the first portion 142 and the second portion 144 overlap.

The method further optionally includes treating a portion of the sheath 112 with a third treatment. For instance, the third treatment includes removing at least a portion or all of the second treatment, such as the chemical etch. For instance, at least a portion 146 of the interface is treated with a third treatment to remove the second treatment such as the chemical etch. In an option, the third treatment includes mechanically treating the portion 146, such as by buffing, blasting, or otherwise treating the portion 146. In still another option, the sheath 112 is masked prior to the second treatment, such as the chemical etch to control where the chemical etch occurs.

It should be noted that the relative lengths and locations of the first portion 142, the second portion 144, and the portion 146 can be varied, and the amount of overlap can be varied. For example, the amount of overlap can be varied to achieve a sufficient amount of attachment between the handle assembly and the sheath 112, without interfering with the ability of the sheath to be split and removed from around a device therein.

The method further optionally includes coupling a handle assembly with the sheath at the surface treated interface. For instance, material is flowed over the sheath proxial end to connect the handle assembly to the handle interface. In an option, the material is flowed through flow holes 119 (FIG. 3) of the handle interface.

Advantageously, the introducer assembly described above provides many benefits. For example, the introducer assembly allows for a sheath, such as a slippery sheath, to be effectively bonded with a handle assembly, and further provides a seal between the sheath and the handle. For example, a seal is provided when the sheath is chemically bonded with the handle assembly. Furthermore, the methods and coupling techniques increase the tensile strength of the sheath to handle the bonding of the sheath and the handle assembly. In addition, the chemically etched sheath can withstand higher temperatures, for example temperatures in certain manufacturing procedures, such as, but not limited to during overmolding processes. The introducer assembly further allows for removal of the introducer without disruption to the procedure or placement of the medical device such as a lead.

It is to be understood that the above description is intended to be illustrative, and not restrictive. Many other embodiments will be apparent to those of skill in the art upon reading and understanding the above description. It should be noted that embodiments or portions thereof discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. A method for forming an introducer sheath, the method comprising:
 a) providing a first lubricious polymeric tube comprising a sheath extending from a sheath proximal end portion to a sheath distal end portion with an intermediate portion therebetween, the sheath having a first passage therethrough;
 b) providing a handle assembly of a second lubricious polymeric material, the handle assembly comprising a second passage having an inner surface;
 c) mechanically surface treating at least one of the sheath proximal end portion and the inner surface of the handle assembly, thereby forming an interface at the mechanical surface treatment, wherein the mechanically surface treated interface is of a substantially constant outer diameter at the sheath proximal end portion and of a substantially constant inner diameter at the inner surface of the handle assembly; and
 d) bonding the second polymeric material of the handle assembly to the first polymeric tube comprising the sheath, thereby forming an airtight seal between the inner surface of the handle assembly and the sheath proximal end portion at the mechanically surface treated interface with the first and second passages being in aligned communication with each other.

2. The method as recited in claim 1 wherein mechanically surface treating includes mechanically etching at least one of the sheath proximal end portion and the inner surface of the handle assembly.

3. The method as recited in claim 2 wherein mechanically etching includes blasting at least one of the sheath proximal end portion and the inner surface of the handle assembly with sodium bicarbonate.

4. The method as recited in claim 1 wherein at least one of the sheath proximal end portion and the inner surface of the handle assembly is further subjected to a chemical etching treatment.

5. The method as recited in claim 4 wherein chemical etching includes etching with sodium naphthalene/ethylene glycol dimethyl ether solution.

6. The method as recited in claim 1 wherein bonding the handle assembly to the sheath includes overmolding the handle assembly on to the sheath.

7. The method as recited in claim 6 wherein overmolding includes flowing the second polymeric material through holes provided in the sheath.

8. The method as recited in claim 1 including chemically etching at least one of the sheath proximal end portion and the inner surface of the handle assembly after the mechanical surface treatment.

9. The method as recited in claim 8, further comprising removing the chemical etching.

10. The method as recited in claim 9, wherein removing the chemical etching includes removing only a portion of the chemical etching.

11. The method as recited in claim. 9, wherein removing the chemical etching includes mechanically removing the chemical etching.

12. The method as recited in claim 8 further comprising masking a portion of the sheath proximal end portion prior to chemically etching there.

13. The method as recited in claim 1 including mechanically surface treating the sheath proximal end portion with one or more of sand, glass, mica, pumice, or dry ice.

14. A method comprising:
a) providing a first lubricious polymeric tube comprising a sheath extending from a sheath proximal end portion to a sheath distal end portion with an intermediate portion therebetween, the sheath having a first passage therethrough;
b) providing a handle assembly of a second lubricious polymeric material, the handle assembly comprising a second passage having an inner surface;
c) mechanically surface treating a first portion of the sheath proximal end portion to thereby form a first textured surface, wherein the first textured surface is of a substantially constant outer diameter at the sheath proximal end portion and of a substantially constant inner diameter at the inner surface of the handle assembly;
d) chemically surface treating a second portion of the sheath proximal end to thereby form a second textured surface, wherein a contact angle of the second textured surface changes from a natural state of 80° to 70° as a result of the chemical treatment, thereby forming an interface at the first and second textured surfaces; and
e) bonding the second polymeric material of the handle assembly to the first polymeric tube comprising the sheath, thereby forming an airtight seal between the inner surface of the handle assembly and the sheath proximal end portion at the interface with the first and second passages being in aligned communication with each other.

15. The method as recited in claim 14 including mechanically surface treating the first portion of the sheath proximal end portion by mechanically etching the first portion.

16. The method as recited in claim 14 including at least partially removing the second textured surface prior to bonding the handle assembly to the sheath at the interface.

17. The method as recited in claim 16 wherein removing the second textured surface includes mechanically treating the second portion of the sheath proximal end portion after it has been chemically treated.

18. The method as recited in claim 14 including treating at least a portion of the sheath proximal end portion with a third treatment.

19. The method as recited in claim 14 including masking at least a portion of the sheath proximal end portion prior to the second, chemical treatment.

20. The method as recited in claim 14 wherein mechanically treating the first portion includes blasting the sheath proximal end portion with sodium bicarbonate.

21. The method as recited in claim 1 including selecting the first polymeric tube and the second polymeric material from the group consisting of PTFE (polytetrafluoroethylene), FEP (fluorinated ethylene-propylene), nylon, polyurethane, polyethylene, polyamide, polypropylene, polyimide, and mixtures thereof.

22. The method as recited in claim 1 including providing the first polymeric tube and the second polymeric material being of either a same or different polymeric material.

23. The method as recited in claim 14 including selecting the first polymeric tube and the second polymeric material from the group consisting of PTFE (polytetrafluoroethylene), FEP (fluorinated ethylene-propylene), nylon, polyurethane, polyethylene, polyamide, polypropylene, polyimide, and mixtures thereof.

24. The method as recited in claim 14 including providing the first polymeric tube and the second polymeric material being of either a same or different polymeric material.

25. A method for forming an introducer sheath, the method comprising:
a) providing a first fluoro-polymeric tube comprising a sheath extending from a sheath proximal end portion to a sheath distal end portion with an intermediate portion therebetween, the sheath having a first passage therethrough;
b) providing a handle assembly of a second fluoro-polymeric material, the handle assembly comprising a second passage having an inner surface;
c) mechanically surface treating at least one of the sheath proximal end portion and the inner surface of the handle assembly, thereby forming an interface at the mechanical surface treatment, wherein the mechanically surface treated interface is of a substantially constant outer diameter at the sheath proximal end portion and of a substantially constant inner diameter at the inner surface of the handle assembly; and
d) bonding the second fluoro-polymeric material of the handle assembly to the first fluoro-polymeric tube comprising the sheath, thereby forming an airtight seal between the inner surface of the handle assembly and the sheath proximal end portion at the mechanically surface treated interface with the first and second passages being in aligned communication with each other.

26. The method of claim 25 including providing at least one of the first and second fluoro-polymeric materials as PTFE.

27. A method for forming an introducer sheath, the method comprising:
a) providing a first lubricious polymeric tube comprising a sheath extending from a sheath proximal end portion to a sheath distal end portion with an intermediate portion therebetween, the sheath having a first passage therethrough;

b) providing a handle assembly of a second lubricious polymeric material, the handle assembly comprising a second passage having an inner surface;

c) mechanically surface treating at least one of the sheath proximal end portion and the inner surface of the handle assembly by blasting with sodium bicarbonate, wherein the mechanically surface treated interface is of a substantially constant outer diameter at the sheath proximal end portion and of a substantially constant inner diameter at the inner surface of the handle assembly; and d) bonding the second polymeric material of the handle assembly to the first polymeric tube comprising the sheath, thereby forming an airtight seal between the inner surface of the handle assembly and the sheath proximal end portion at the mechanically surface treated interface with the first and second passages being in aligned communication with each other.

28. A method for forming an introducer sheath, the method comprising:

a) providing a first lubricious polymeric tube comprising a sheath extending from a sheath proximal end portion to a sheath distal end portion with an intermediate portion therebetween, the sheath having a first passage therethrough;

b) providing a handle assembly of a second lubricious polymeric material, the handle assembly comprising a second passage having an inner surface;

c) mechanically surface treating at least one of the sheath proximal end portion and the inner surface of the handle assembly with one or more of sand, glass, mica, pumice, or dry ice, thereby forming an interface at the mechanical surface treatment, wherein the mechanically surface treated interface is of a substantially constant outer diameter at the sheath proximal end portion and of a substantially constant inner diameter at the inner surface of the handle assembly; and d) bonding the second polymeric material of the handle assembly to the first polymeric tube comprising the sheath, thereby forming an airtight seal between the inner surface of the handle assembly and the sheath proximal end portion at the mechanically surface treated interface with the first and second passages being in aligned communication with each other.

* * * * *